(12) United States Patent
Askari et al.

(10) Patent No.: US 11,998,464 B2
(45) Date of Patent: Jun. 4, 2024

(54) STENT WITH ANGLED STRUTS AND CROWNS

(71) Applicant: Medtronic Vascular, Inc., Santa Rosa, CA (US)

(72) Inventors: Syed Askari, San Jose, CA (US); Richard Bliss, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 161 days.

(21) Appl. No.: 17/382,078

(22) Filed: Jul. 21, 2021

(65) Prior Publication Data

US 2022/0023076 A1    Jan. 27, 2022

Related U.S. Application Data

(60) Provisional application No. 63/056,166, filed on Jul. 24, 2020.

(51) Int. Cl.
*A61F 2/915*   (2013.01)

(52) U.S. Cl.
CPC .... *A61F 2/915* (2013.01); *A61F 2002/91525* (2013.01); *A61F 2220/0058* (2013.01)

(58) Field of Classification Search
CPC .. A61F 2/915; A61F 2/88; A61F 2/885; A61F 2002/91525; A61F 2002/91508; A61F 2002/91516; A61F 2220/0058; A61F 2/91; A61F 2/92
See application file for complete search history.

(56) References Cited

U.S. PATENT DOCUMENTS

| | | | |
|---|---|---|---|
| 5,716,396 | A | 2/1998 | Williams, Jr. |
| 5,948,016 | A | 9/1999 | Jang |
| 6,200,334 | B1 | 3/2001 | Jang |
| 6,235,053 | B1 | 3/2001 | Jang |

(Continued)

FOREIGN PATENT DOCUMENTS

| | | |
|---|---|---|
| EP | 1245203 A2 | 10/2002 |
| FR | 2760351 A1 | 9/1998 |

(Continued)

OTHER PUBLICATIONS

International Search Report and Written Opinion issued in International Application No. PCT/US2021/042907 dated Oct. 28, 2021.

(Continued)

*Primary Examiner* — Brooke Labranche
(74) *Attorney, Agent, or Firm* — Medler Ferro Woodhouse & Mills PLLC (57) ABSTRACT

A stent in a radially compressed configuration includes a plurality of first outer crowns and a plurality of second outer crowns, each of the first outer crowns and the second outer crowns connected by a strut of a plurality of struts. The plurality of first outer crowns and the plurality of second outer crowns are disposed at a crown angle in the range of about 15 degrees to about 35 degrees, the crown angle being defined by a line extending through a midpoint of a crown of the plurality of first outer crowns or the plurality of second outer crowns through a center of radius of the crown with respect to a line that is parallel to a central longitudinal axis of the stent.

7 Claims, 6 Drawing Sheets

(56) References Cited

U.S. PATENT DOCUMENTS

| | | |
|---|---|---|
| 6,398,805 B1 | 6/2002 | Alt |
| 6,491,718 B1 | 12/2002 | Ahmad |
| 6,602,285 B1 | 8/2003 | Von Oepen et al. |
| 6,682,554 B2 | 1/2004 | Von Oepen et al. |
| 6,755,856 B2 | 6/2004 | Fierens et al. |
| 6,776,794 B1 | 8/2004 | Hong et al. |
| 6,814,749 B2 | 11/2004 | Cox et al. |
| 6,821,292 B2 * | 11/2004 | Pazienza ............... A61F 2/915 623/1.22 |
| 6,881,222 B2 | 4/2005 | White et al. |
| 6,939,373 B2 | 9/2005 | Gomez et al. |
| 7,128,756 B2 | 10/2006 | Lowe et al. |
| 7,179,285 B2 | 2/2007 | Ikeuchi et al. |
| 7,329,277 B2 | 2/2008 | Addonizio et al. |
| 7,404,823 B2 | 7/2008 | Gregorich et al. |
| 7,491,227 B2 | 2/2009 | Yang et al. |
| 7,618,445 B2 | 11/2009 | Moriuchi et al. |
| 7,625,401 B2 | 12/2009 | Clifford et al. |
| 7,645,297 B2 | 1/2010 | Nissl |
| 7,651,524 B2 | 1/2010 | Moriuchi et al. |
| 7,691,142 B2 | 4/2010 | Nissl |
| 7,803,179 B2 | 9/2010 | Denison |
| 7,879,084 B2 | 2/2011 | Goto |
| 7,887,578 B2 | 2/2011 | Schneider |
| 7,972,373 B2 | 7/2011 | Contiliano et al. |
| 7,981,149 B2 | 7/2011 | Contiliano et al. |
| 7,985,251 B2 | 7/2011 | Ikeuchi et al. |
| 8,016,876 B2 | 9/2011 | Gregorich et al. |
| 8,043,358 B2 | 10/2011 | Weber et al. |
| 8,048,142 B2 | 11/2011 | Venturelli |
| 8,070,792 B2 | 12/2011 | Gregorich et al. |
| 8,105,373 B2 | 1/2012 | Girton et al. |
| 8,109,991 B2 | 2/2012 | Clifford et al. |
| 8,147,538 B2 | 4/2012 | Brown et al. |
| 8,157,858 B2 | 4/2012 | Goto |
| 8,287,587 B2 | 10/2012 | Moriuchi |
| 8,303,645 B2 | 11/2012 | Von Oepen et al. |
| 8,323,331 B2 | 12/2012 | Dreher |
| 8,337,544 B2 | 12/2012 | Osman et al. |
| 8,348,991 B2 | 1/2013 | Weber et al. |
| 8,430,924 B2 | 4/2013 | Ehr et al. |
| 8,449,596 B2 | 5/2013 | Goto |
| 8,523,935 B2 | 9/2013 | Fliedner |
| 8,523,938 B2 | 9/2013 | Takeuchi et al. |
| 8,556,959 B2 | 10/2013 | Goto |
| 8,562,665 B2 | 10/2013 | Jang |
| 8,585,752 B2 | 11/2013 | Sudo et al. |
| 8,608,794 B2 | 12/2013 | Girton et al. |
| 8,652,196 B2 | 2/2014 | Nissl |
| 8,721,705 B2 | 5/2014 | White et al. |
| 8,728,146 B2 | 5/2014 | Gregorich et al. |
| 8,740,967 B2 | 6/2014 | Mitsudo et al. |
| 8,882,824 B2 | 11/2014 | Kim et al. |
| 8,916,226 B2 | 12/2014 | Mauch et al. |
| 8,920,488 B2 | 12/2014 | Bregulla |
| 8,986,366 B2 | 3/2015 | Girton et al. |
| 9,095,459 B2 | 8/2015 | Maruyama et al. |
| 9,265,636 B2 * | 2/2016 | Chanduszko ........... A61F 2/915 |
| 9,445,927 B2 | 9/2016 | Lee et al. |
| 9,526,643 B2 | 12/2016 | Goto |
| 9,603,732 B2 | 3/2017 | Ma et al. |
| 9,801,743 B2 | 10/2017 | Kreidler et al. |
| 9,827,120 B2 | 11/2017 | Gregorich et al. |
| 10,327,926 B2 | 6/2019 | Lee et al. |
| 10,420,637 B2 | 9/2019 | Fierens et al. |
| 10,420,660 B2 | 9/2019 | Shobayashi |
| 10,603,194 B2 | 3/2020 | Zhao et al. |
| 2001/0047200 A1 | 11/2001 | White et al. |
| 2003/0014102 A1 | 1/2003 | Hong et al. |
| 2003/0144731 A1 | 7/2003 | Wolinsky et al. |
| 2006/0004436 A1 | 1/2006 | Amarant et al. |
| 2006/0060266 A1 | 3/2006 | Bales et al. |
| 2006/0100690 A1 | 5/2006 | Venturelli |
| 2007/0016283 A1 | 1/2007 | Greenhalgh et al. |
| 2007/0078511 A1 | 4/2007 | Ehr et al. |
| 2007/0208411 A1 | 9/2007 | Meyer et al. |
| 2008/0281407 A1 | 11/2008 | Addonizio et al. |
| 2008/0294267 A1 | 11/2008 | Chanduszko |
| 2009/0093869 A1 | 4/2009 | Cunniffe et al. |
| 2009/0105809 A1 | 4/2009 | Lee et al. |
| 2010/0094405 A1 | 4/2010 | Cottone |
| 2010/0131044 A1 | 5/2010 | Patel |
| 2010/0204780 A1 | 8/2010 | Fliedner et al. |
| 2011/0054592 A1 | 3/2011 | Fliedner |
| 2011/0166641 A1 | 7/2011 | Bales, Jr. et al. |
| 2011/0218614 A1 | 9/2011 | Lam |
| 2013/0282107 A1 * | 10/2013 | Baldwin ............... B23K 26/361 623/1.22 |
| 2013/0317595 A1 * | 11/2013 | Obradovic ................ A61F 2/07 623/1.13 |
| 2013/0345790 A1 | 12/2013 | Cottone |
| 2016/0206451 A1 | 7/2016 | Maruyama |
| 2018/0360628 A1 | 12/2018 | Yan et al. |
| 2019/0254847 A1 | 8/2019 | Lee et al. |

FOREIGN PATENT DOCUMENTS

| | | |
|---|---|---|
| WO | 2011/034795 A1 | 3/2011 |
| WO | 2012/096716 A2 | 7/2012 |
| WO | 2017/168196 A1 | 10/2017 |

OTHER PUBLICATIONS

International Search Report and Written Opinion issued in International Application No. PCT/US2021/042918 dated Oct. 29, 2021.

* cited by examiner

STENT WITH ANGLED STRUTS AND CROWNS

CROSS-REFERENCE TO RELATED APPLICATIONS

This application claims the benefit of the filing date of U.S. Provisional Application No. 63/056,166, filed Jul. 24, 2020, the contents of which are incorporated herein by reference in their entirety.

FIELD OF THE INVENTION

This invention generally relates to endoluminal prostheses or stents. More specifically, the invention relates to stents with angled struts.

BACKGROUND OF THE INVENTION

A stent is a type of endoluminal prosthesis. Stents are generally tubular open-ended structures providing support for damaged, collapsing, or occluded blood vessels. They are radially expandable from a radially compressed configuration for delivery to the affected vessel site to a radially expanded configuration when deployed at the affected vessel treatment site, with the radially expanded configuration having a larger diameter than the radially compressed configuration. Stents are generally inserted in the radially compressed configuration and expanded to the radially expanded configuration either through a self-expanding mechanism, or through the use of a balloon catheter or other mechanical expansion.

BRIEF SUMMARY OF THE INVENTION

The design of a stent must balance several characteristics. For example, and not by way of limitation, characteristics such as stent distortion, radial strength, overexpansion, crossing profile, flexibility, strut/crown lift, retention, metal to artery ratio, drug load, and retention are some of the many characteristics used to drive optimization and design decisions. For example, using thinner profile struts while keeping other variables the same for a given design, the radial strength of the stent decreases and risk of strut/crown lifting and stent retention increase. If the thinner profile strut is paired with a decrease in strut lengths to maintain a similar radial strength, then the ability of the struts and crowns to open (referred to as overexpansion) is compromised. Thinner struts are generally desirable for improved flexibility, deliverability, and a prevailing belief that thinner struts improve lesion healing. Strut/crown lifting (or stent lifting) is when either a crown or strut or multiple crowns and struts are lifted out of plane which would give an appearance those crowns/struts being lifted away from the delivery system. This is seen as deformation of the crowns/struts outward in the radial direction. Stent distortion is deformation of the stent along the long axis of the stent.

Accordingly, there is a need for improved stent designs that enable improved characteristics of the stent.

Embodiments hereof are directed to a stent including a radially compressed configuration and a radially expanded configuration. The stent in the radially compressed configuration includes a plurality of first outer crowns and a plurality of second outer crowns, each of the first outer crowns and the second outer crowns connected by a strut of a plurality of struts. The plurality of first outer crowns and the plurality of second outer crowns are disposed at a crown angle in the range of about 15 degrees to about 35 degrees. The crown angle is defined by a line extending through a midpoint of a crown of the plurality of first outer crowns or the plurality of second outer crowns through a center of radius of the crown with respect to a line that is parallel to a central longitudinal axis of the stent.

Embodiments hereof are also directed to a stent according to any of the embodiments herein, wherein the crown angle is in the range of about 25 degrees to about 30 degrees.

Embodiments hereof are also directed to a stent according to any of the embodiments herein, wherein the stent is a continuous wire stent comprising a wire bent into a waveform wrapped into a plurality of bands, the waveform including the plurality of first outer crowns, the plurality of second outer crowns, and the plurality of struts.

Embodiments hereof are also directed to a stent according to any of the embodiments herein, further comprising connections between adjacent bands of the plurality of bands.

Embodiments hereof are also directed to a stent according to any of the embodiments herein, wherein each connection is between one of the plurality of first crowns of a band of the plurality of bands and one of the plurality of second crowns of an adjacent band of the plurality of bands.

Embodiments hereof are also directed to a stent according to any of the embodiments herein, wherein the connections are fused connections, welded connections, or soldered connections.

Embodiments hereof are also directed to a stent according to any of the embodiments herein, wherein the stent is a laser cut stent.

Embodiments hereof are also directed to a stent according to any of the embodiments herein, wherein the stent includes a plurality of bands including the plurality of first outer crowns, the plurality of second outer crowns, and the plurality of struts.

Embodiments hereof are also directed to a stent according to any of the embodiments herein, further comprising connections between adjacent bands of the plurality of bands.

Embodiments hereof are also directed to a stent according to any of the embodiments herein, wherein each connection is between one of the plurality of first crowns of a band of the plurality of bands and one of the plurality of second crowns of an adjacent band of the plurality of bands.

Embodiments hereof are also directed to a stent according to any of the embodiments herein, wherein the connections are elongated.

Embodiments hereof are also directed to a stent including a radially compressed configuration and the radially expanded configuration. The stent in the radially compressed configuration includes a plurality of first outer crowns and a plurality of second outer crowns, each of the first outer crowns and the second outer crowns connected by a strut of a plurality of struts. The plurality of first outer crowns includes angled first outer crowns and parallel first outer crowns and the plurality of second outer crowns includes angled second outer crowns and parallel second outer crowns. The angled first outer crowns and the angled second outer crowns are disposed at a crown angle in the range of about 15 degrees to about 35 degrees. The crown angle is defined by a line extending through a midpoint of a crown of the angled first outer crowns or the angled second outer crowns through a center of radius of the crown with respect to a line that is parallel to a central longitudinal axis of the stent. The parallel first outer crowns and the parallel second outer crowns are disposed parallel to the central longitudinal axis of the stent.

Embodiments hereof are also directed to a stent according to any of the embodiments herein, wherein the crown angle is in the range of about 25 degrees to about 30 degrees.

Embodiments hereof are also directed to a stent according to any of the embodiments herein, further comprising a plurality of mid-crowns, each mid-crown disposed between a parallel first outer crown of the parallel first outer crowns and an angled second outer crown of the angled second outer crowns or a parallel second outer crown of the parallel second outer crowns and an angled first outer crown of the angled first outer crowns.

Embodiments hereof are also directed to a stent according to any of the embodiments herein, wherein the stent includes a plurality of bands including the plurality of first outer crowns, the plurality of second outer crowns, and the plurality of struts.

Embodiments hereof are also directed to a stent according to any of the embodiments herein, further comprising connections between adjacent bands of the plurality of bands.

Embodiments hereof are also directed to a stent according to any of the embodiments herein, wherein each connection is between one of the parallel first outer crowns a band of the plurality of bands and one of the parallel second outer crowns of an adjacent band of the plurality of bands.

Embodiments hereof are also directed to a stent according to any of the embodiments herein, wherein the stent is a continuous wire stent and the plurality of connections are fused connections, welded connections, or soldered connections.

Embodiments hereof are also directed to a stent according to any of the embodiments herein, wherein the stent is a laser cut stent and the plurality of connections are elongated.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

The following detailed description is merely exemplary in nature and is not intended to limit the invention or the application and uses of the invention. Although the description of the invention is in the context of treatment of blood vessels, the invention may also be used in any other body passageways where it is deemed useful. Furthermore, there is no intention to be bound by any expressed or implied theory presented in the preceding technical field, background, brief summary or the following detailed description.

The term "continuous wire stent" as used herein means a stent form by from a wire that is bent into a waveform and helically wrapped around a central longitudinal axis to form a tube. Stents that are formed, e.g., by laser cutting a tube to removed portions such that the portions that are not removed from the stent are not "continuous wire stents".

As used herein the term "crown" is a turn or bend in a wire or stent element.

As used herein the term "strut" is a generally straight portion of a wire or stent element connecting two crowns together.

Figure 1:
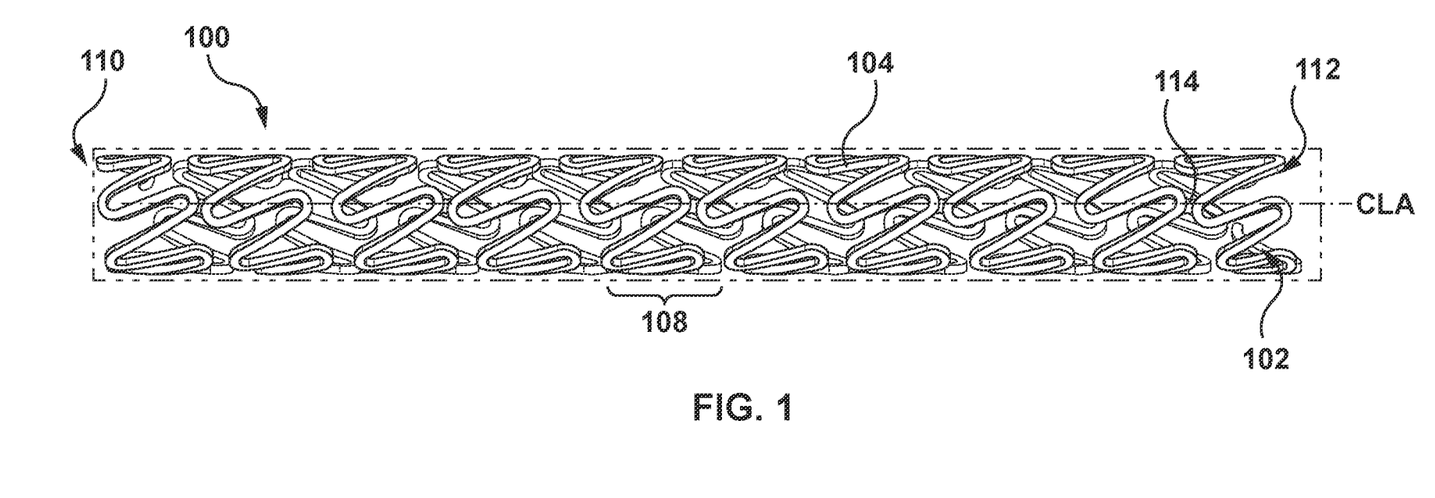
FIG. 1 is a perspective view of a continuous wire stent in a radially compressed configuration according to an embodiment hereof.

FIGS. 1-4 illustrate a stent 100 according to an embodiment hereof. The stent 100 includes a radially compressed configuration for delivery to the affected site of a blood vessel, as shown in FIG. 1, and a radially expanded configuration when deployed (not shown). The stent 100 is a generally tubular, open-ended structure having a first end 110 and a second end 112, and defines a lumen 102 therethrough. The stent 100 may be self-expanding or balloon expandable. In the embodiment of FIGS. 1-4, the stent 100 is a continuous wire stent formed from a wire 104 formed into a waveform and then helically wrapped (such as around a mandrel) to form the stent 100. Other steps in processing the wire 104 and/or the stent 100 may also be included. For example, and not by way of limitation, the wire 104 may be swaged prior to or after forming the wire 104 into the waveform. Swaging the wire 104 reduces the overall cross-section or diameter of the wire 104. Other steps such as connections between adjacent bands in the wrapped waveform, as explained in more detail below, polishing and other finishing steps may also be used in forming the stent 100.

Figure 3:
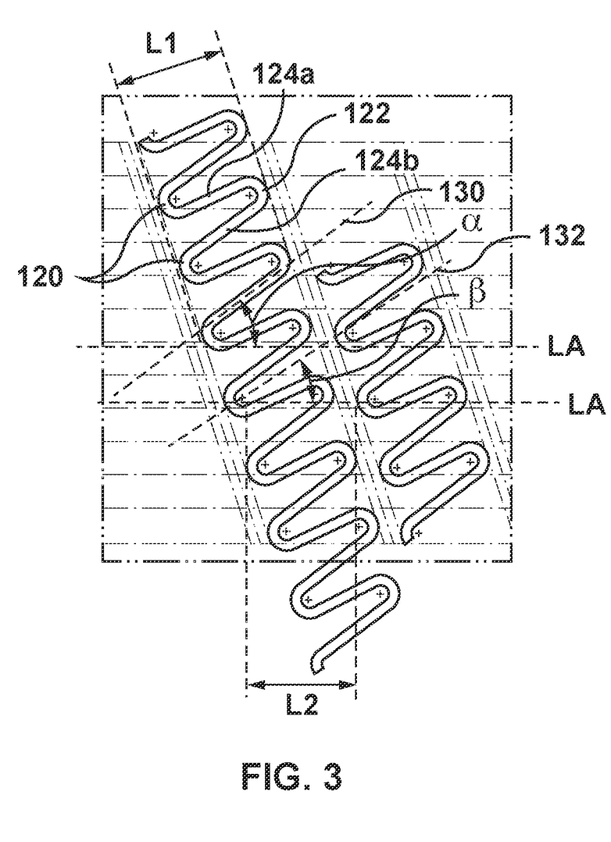
FIG. 3 illustrates a flat layout of a portion of the continuous wire stent of FIG. 1.

The wire 104 is a continuous element or strand that is bent into the waveform, as shown in FIG. 3, and is wrapped into a helix having a plurality of windings, turns, or bands 108 that form a hollow cylindrical shape of the overall stent 100. A "winding", "turn", or "band" as used herein is complete (360 degree) wrap of the wire 104 around a central longitudinal axis of the stent. FIG. 1 shows ten bands 108 of the stent 100, but the stent 100 may include more or fewer bands 108. The bands 108 are generally angled with respect to a central longitudinal axis CLA of the stent 100 such that the bands or windings 108 are not perpendicular to the central longitudinal axis CLA.

The waveform shown in FIG. 3 is the waveform for the central portion of the stent 100, and may also be used for the end portions of the stent. As best shown in FIG. 3, the waveform generally includes a repeating series of a first outer bend or crown 120 and a second outer bend or crown 122. The inner curve or intrados of the first outer crown 120 faces the inner curve or intrados of the second outer crown 122 such that the first outer crown 120 turns the wave towards the second outer crown 122 and the second outer crown 122 turns the wave towards the first outer crown 120. In other words, the inner curve or intrados of the first outer crown 120 faces the second end 112 of the stent 100 and the inner curve or intrados of the second outer crown 122 faces the first end 110 of the stent 100. A first strut 124a connects the first outer crown 120 to the second outer crown 122. A second strut 124b connects the second outer crown 122 to the first outer crown 120 in the next wave of the waveform. The first and second struts 124a, 124b may also be generally referred to as struts 124. Thus, a complete wave of the waveform in a particular order starting from one of the first outer crowns 120 is the first outer crown 120, the first strut 124a, the second outer crown 122 turning the wave in a generally opposite direction, and the second strut 124b connecting to another first crown 120 in the next wave of the waveform. This pattern repeats itself at least though the central portion of the stent 100.

Figure 2:
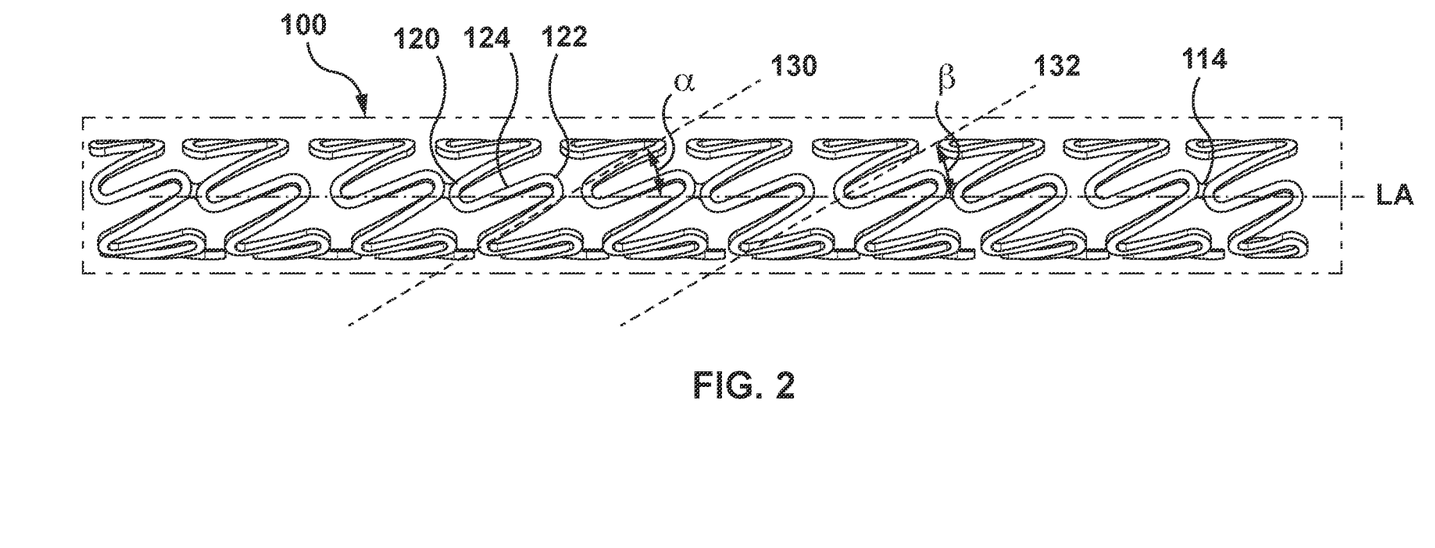
FIG. 2 is a sectional view of the continuous wire stent of FIG. 1.

In the embodiment of FIGS. 1-4, the waveform of the stent 100 is configured such that when the waveform is wrapped to form the stent 100, the struts 124 are disposed at an angle α with respect to the a longitudinal line LA that is parallel to the central longitudinal axis CLA of the stent 100. Thus, a line 130 that extends parallel to a strut 124 is at the angle α with respect to the line LA. Similarly, a line 132 that extends through the middle of the extrados, the middle of the intrados, and the center of radius one of the crowns 120, 122 is disposed at an angle β with respect to a line LA that is parallel central longitudinal axis CLA of the stent 100. A corresponding line 132 exists for each of the crowns 120, 122 such that each of the crowns 120, 122 are disposed at the angle β with respect to a line that is parallel to the central longitudinal axis CLA of the stent 100. As can be seen in FIGS. 2 and 3, those skilled in the art will recognize that the line LA can be the same line or different lines that are parallel to the central longitudinal axis LA. The angle α and the angle β are approximately the same, but not necessarily exactly the same. In embodiments, the angles α and β are within about 8 degrees of each other. The angles α and β are each in the range of about 15 degrees to about 35 degrees, and preferably in the range of about 25 degrees to about 30 degrees.

As noted in the Summary of the Invention section above, a trade-off in using thinner profile struts (wire) in a stent is the increased risk of stent lifting and stent distortion, and reduced stent retention. However, using the highly angled struts 124 and crowns 120, 122 described above, stent lifting and stent distortion may be reduced. As can be seen in FIG. 3, a length L1 from one of the first outer crowns 120 to an adjacent one of the second outer crowns 122 along a strut 124 is greater than a longitudinal length L2 from the first outer crown 120 to the second outer crown 122, the longitudinal length L2 being defined as parallel to the central longitudinal axis CLA of the stent 100. This shortened longitudinal length L2 increases resistance to forces that may result in stent lifting, stent distortion, and/or poor stent retention, while maintaining the overall sinusoidal length of each band 108 such that stent overexpansion is not compromised.

Figure 4:
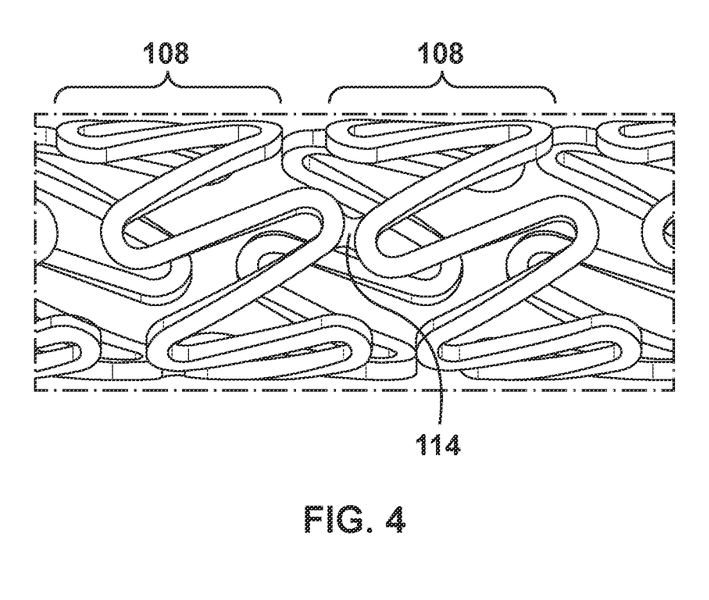
FIG. 4 illustrates a portion of the continuous wire stent of FIG. 1.

Referring to FIGS. 2 and 4, the stent 100 also includes a plurality of connections 114 that are configured to connect selected outer crowns of 120, 122 of a band 108 with selected outer crowns 122, 120 of an adjacent band 108. The connections 114 may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Further, a repeating body unit is defined between adjacent connections 114 along the helical path of the bands 108. Using repeating body units for at least portions of the continuous wire stent 100 enables the stent 100 to be easily varied in length. In particular, the wire 104 formed into the waveform may include enough repeating body units for a multiple of continuous wire stents. Depending on the desired length of the stent 100, the wire 104 may be cut with more or less repeating body units. Therefore, instead of a waveform of a particular length made for each length stent, the wire 104 may be bent into one waveform and then be cut for different stent lengths.

In embodiments, not shown, the first end 110 and/or the second end 112 of the stent 100 may be formed such as to be substantially orthogonal to the central longitudinal axis CLA. Details regarding how the first end 110 and/or second end 112 of the stent 100 may be substantially orthogonal to the central longitudinal axis CLA can be found in U.S. Pat. No. 9,060,889, assigned to Medtronic Vascular, Inc., which is incorporated by reference herein in its entirety.

Figure 5:
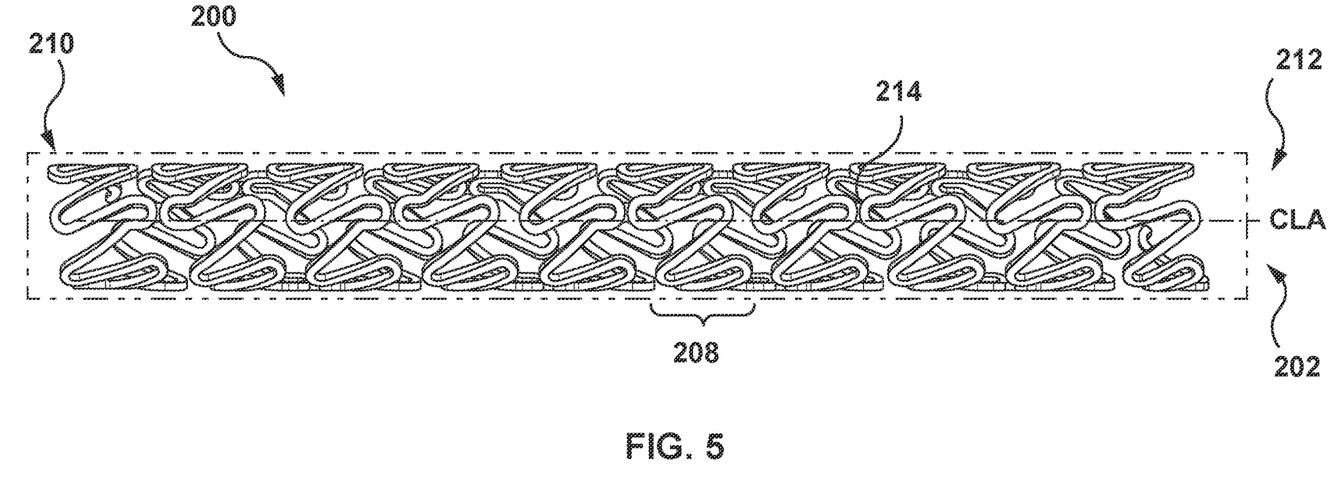
FIG. 5 is a perspective view of a continuous wire stent in a radially compressed configuration according to an embodiment hereof.

FIGS. 5-8 illustrate a stent 200 according to another embodiment hereof. The stent 200 includes a radially compressed configuration for delivery to the affected site of a blood vessel, as shown in FIG. 5, and a radially expanded configuration when deployed (not shown). The stent 200 is a generally tubular, open-ended structure having a first end 210 and a second end 212, and defines a lumen 202 therethrough. The stent 200 may be self-expanding or balloon expandable. In the embodiment of FIGS. 5-8, the stent 200 is a continuous wire stent formed from a wire 204 formed into a waveform and then helically wrapped (such as around a mandrel) to form the stent 200. Other steps in processing the wire 204 and/or the stent 200 may also be included. For example, and not by way of limitation, the wire 204 may be swaged prior to or after forming the wire 204 into the waveform. Swaging the wire 204 reduces the overall cross-section or diameter of the wire 204. Other steps such as connections between adjacent bands in the wrapped waveform, as explained in more detail below, polishing and other finishing steps may also be used in forming the stent 200.

Figure 7:
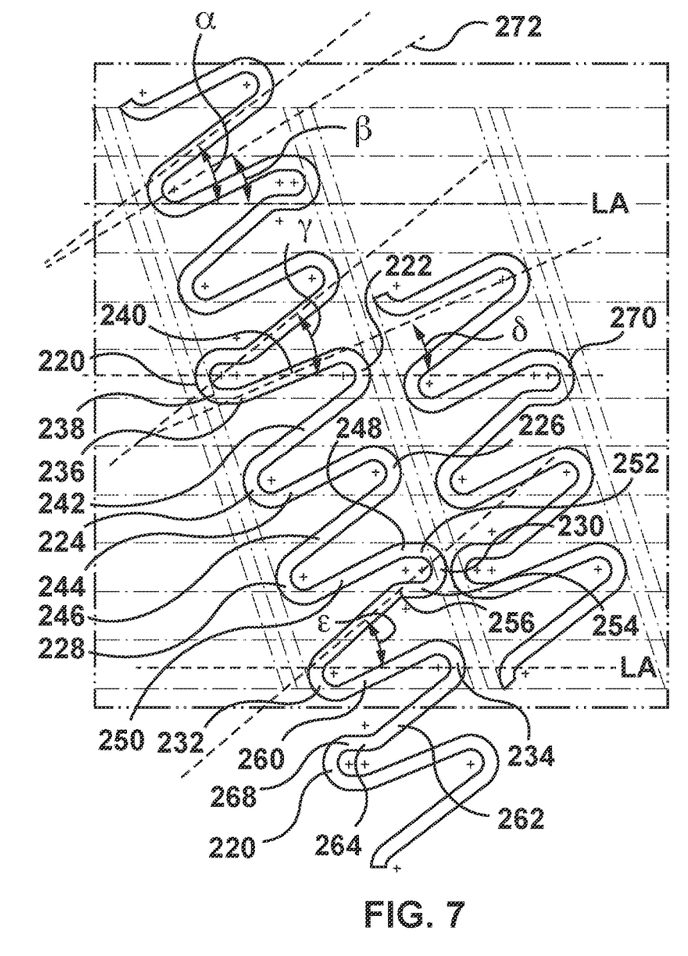
FIG. 7 illustrates a flat layout of a portion of the continuous wire stent of FIG. 5.

The wire 204 is a continuous element or strand that is bent into the waveform, as shown in FIG. 7, and is wrapped into a helix having a plurality of windings, turns, or bands 208 that form a hollow cylindrical shape of the overall stent 200. FIG. 5 shows eleven bands 208 of the stent 200, but the stent 200 may include more or fewer bands 208. The bands 208 are generally angled with respect to a central longitudinal axis CLA of the stent 200 such that the bands or windings 208 are not perpendicular to the central longitudinal axis CLA.

Figure 9:
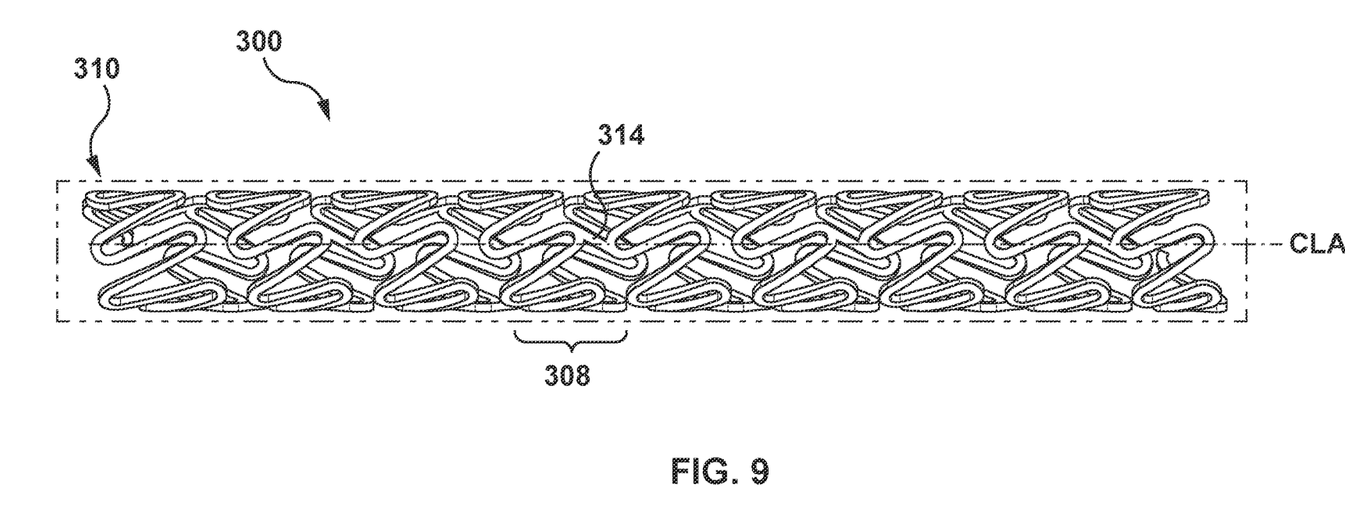
FIG. 9 is a perspective view of a stent in a radially compressed configuration according to an embodiment hereof.

The waveform shown in FIG. 7 is the waveform for the central portion of the stent 200, and may also be used for the end portions of the stent. As best shown in FIG. 9, the waveform generally includes a repeating series of a parallel first outer bend or crown 220, an angled second outer bend or crown 222, an angled third outer bend or crown 224, an angled fourth outer bend or crown 226, an angled fifth outer bend or crown 228, a parallel sixth outer bend or crown 230, an angled seventh outer bend or crown 232, and an angled eighth outer bend or crown 234. The waveform then repeats starting with another parallel first outer bend or crown 220.

The inner curve or intrados of the first, third, fifth, and seventh outer crowns 220, 224, 228, 232 generally face the inner curve or intrados of the second, fourth, sixth, and eighth outer crowns 222, 226, 230, and 234 such that the first, third, fifth, and seventh outer crowns 220, 224, 228, 232 turn the wave towards the second, fourth, sixth, and eighth outer crowns 222, 226, 230, 234, respectively, and vice versa. In other words, the inner curves or intrados of the first, third, fifth, and seventh outer crowns 220, 224, 228, 232 face the second end 212 of the stent 200 and the inner curves or intrados of the second, fourth, sixth, and eighth outer crowns 222, 226, 230, and 234 face the first end 210 of the stent 200. The "parallel outer crowns" 220 and 230 are defined by a respective line 270 that extends through the middle of the extrados, the middle of the intrados, and the center of radius of the respective crown 220, 230 being parallel to the central longitudinal axis CLA of the stent 200, as shown in FIG. 7. As explained in more detail below, the parallel outer crowns 220, 230 are formed by mid-crowns between adjacent outer crowns. The "angled outer crowns" 222, 224, 226, 228, 232, 234 are defined by a respective line 272 that extends through the middle of the extrados, the middle of the intrados, and the center of radius of the respective crown 222, 224, 226, 228, 232, 234 being disposed at an angle $\beta$ with respect to a line LA that is parallel to the central longitudinal axis CLA of the stent 200, as shown in FIG. 7.

Continuing with the description of the waveform, a first mid-crown 236 is disposed between the parallel first outer crown 220 and the angled second outer crown 222. A parallel first strut 238 connects the parallel first outer crown 220 to the first mid-crown 236 and an angled second strut 240 connects the first mid-crown 236 to the angled second outer crown 222. The parallel first strut 238 is generally parallel to the central longitudinal axis CLA of the stent 200 and the angled second strut 240 is disposed at an angle with respect to a line LA that is parallel to the central longitudinal axis CLA of the stent 200. Thus, the first mid-crown 236 serves to transition from the parallel first strut 238 to the angled second strut 240. Continuing with the waveform, an angled third strut 242 connects the angled second outer crown 222 to the angled third outer crown 224, and an angled fourth strut 244 connects the angled third outer crown 224 to the angled fourth outer crown 226, and an angled fifth strut 246 connects the angled fourth outer crown 226 to the angled fifth outer crown 228. A second mid-crown 248 is disposed between the angled fifth outer crown 228 and the parallel sixth outer crown 230. An angled sixth strut 250 connects the angled fifth outer crown 228 to the second mid-crown 248 and a parallel seventh strut 252 connects the second mid-crown 248 to the parallel sixth outer crown 230. The second mid-crown 248 serves to transition from the angled sixth strut 250 to the parallel seventh strut 252 such that the sixth outer crown 230 may be a parallel outer crown. Continuing with the waveform, a third mid-crown 248 is disposed between the parallel sixth outer crown 230 and the angled seventh outer crown 232. A parallel eighth strut 254 connects the parallel sixth outer crown 230 to the third mid-crown 256 and an angled ninth strut 258 connects the third mid-crown 256 to the angled seventh outer crown 232. The third mid-crown 256 serves to transition from the parallel eighth strut 254 to the angled ninth strut 258 such that the seventh outer crown 232 may be an angled outer crown.

Continuing with the waveform, an angled tenth strut 260 connects the angled seventh outer crown 232 to the angled eighth outer crown 234. A fourth mid-crown 264 is disposed between the angled eighth outer crown 234 and the parallel first outer crown 220 that begins the next wave of the waveform. An angled eleventh strut 262 connects the angled eighth outer crown 234 to the fourth mid-crown 264 and a parallel twelfth strut 268 connects the fourth mid-crown 264 to the parallel first outer crown 220 of the next wave of the waveform. The fourth mid-crown 264 serves to transition from the angled eleventh strut 262 to the parallel twelfth strut 268 such that the first outer crown 220 in the next wave of the waveform may be a parallel outer crown.

As explained above, the angled outer crowns are disposed at an angle $\beta$ with respect to a line LA parallel to the central longitudinal axis of the stent 200 and the parallel crowns are disposed parallel to the central longitudinal axis CLA of the stent 200. The angle $\beta$ is in the range of about 15 degrees to about 35 degrees, and preferably in the range of about 25 degrees to about 30 degrees.

Similarly, the angled struts noted above are disposed at an angle with respect to a line LA that is parallel to the central longitudinal axis CLA of the stent 200. The angles of the angled struts may vary depending on the type of strut. For example, and not by way of limitation, an angled strut disposed between two angled outer crowns, such as the angled third strut 242 may be disposed at an angle $\alpha$ with respect to a line LA parallel to the central longitudinal axis CLA of the stent 200. Similarly, the angled struts disposed between parallel outer crowns facing the second end 212 of the stent 200 and angled outer crowns facing the first end 210 of the stent 200, each with a mid-crown disposed therebetween, such as the eleventh angled strut 262 and the second angled strut 240, may be disposed at an angles $\gamma$ and $\delta$, respectively, with respect to a line LA parallel to the central longitudinal axis CLA of the stent 200. Similarly, an angled strut disposed between a parallel outer crown facing the first end 210 of the stent 200 and an angled crown facing the second end 212 of the stent 200, such as the angled ninth strut 258, may be disposed at an angle $\varepsilon$ with respect to a line LA parallel to a central longitudinal axis CLA of the stent 200. The angles $\alpha$, $\gamma$, $\delta$, and $\varepsilon$ need not be the same angle, but each may be in the range of about 15 degrees to about 35 degrees, and preferably in the range of about 25 degrees to about 30 degrees.

Figure 6:
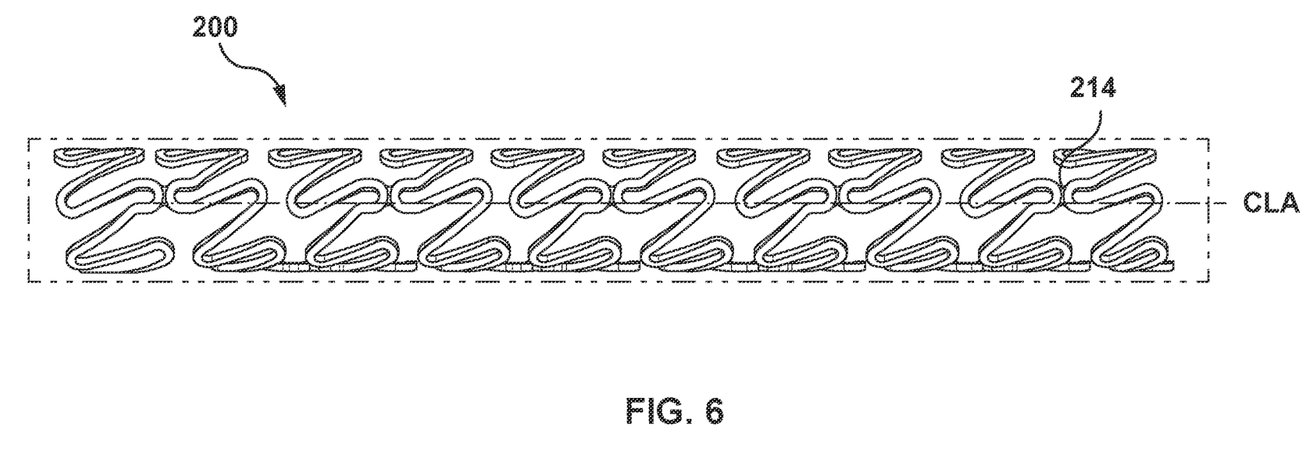
FIG. 6 is a sectional view of the continuous wire stent of FIG. 5.
Figure 8:
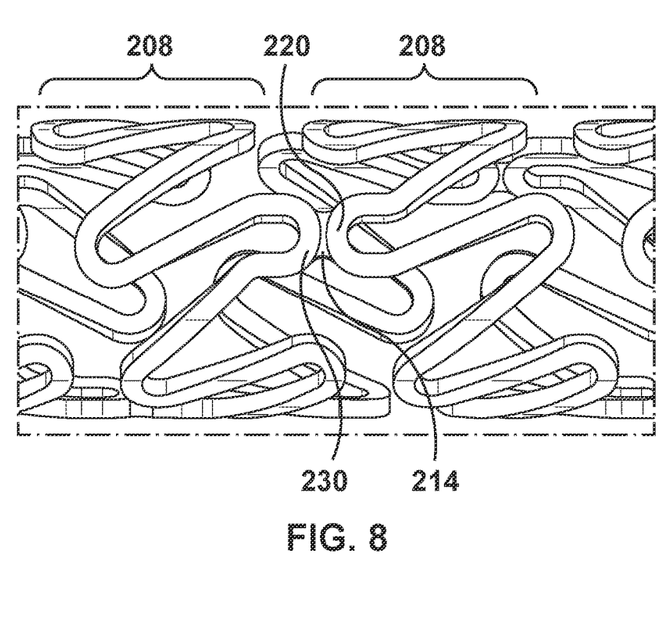
FIG. 8 illustrates a portion of the continuous wire stent of FIG. 5.

Referring to FIGS. 5, 6, and 8, the stent 200 also includes a plurality of connections 214 that are configured to connect parallel outer crowns 220, 230 of a band 208 with parallel outer crowns 230, 220 of an adjacent band 208. The connections 214 may be created, for example and not by way of limitation, by fusing, welding, or soldering the selected outer crowns together. As used herein, "welding" and "soldering" are defined as heating an additional material that is separate from the selected outer crowns and applying the heated additional material to the selected outer crowns so that when the additional material cools, the selected outer crowns are welded or soldered together. Having connections 214 between parallel outer crowns 214, as shown in FIG. 8, rather than angled outer crowns, as shown in FIG. 4, provides for better alignment of the outer crowns being connected, thereby providing a better connection 214 as compared to the connection 114.

Further, a repeating body unit is defined between adjacent connections 214 along the helical path of the bands 208. Using repeating body units for at least portions of the continuous wire stent 200 enables the stent 200 to be easily varied in length. In particular, the wire 204 formed into the waveform may include enough repeating body units for a multiple of continuous wire stents. Depending on the desired length of the stent 200, the wire 204 may be cut with more or less repeating body units. Therefore, instead of a waveform of a particular length made for each length stent, the wire 204 may be bent into one waveform and then be cut for different stent lengths.

Using a combination of angled outer crowns and parallel outer crowns, as shown in FIGS. 5-8, enables the advantages described above with respect to FIGS. 1-4 of reducing the risk of stent lifting and stent distortion, while also enabling the connections 214 to be made between parallel outer crowns 220, 230 for better alignment. As discussed above with respect to FIGS. 1-4, a length from an outer crown facing the second end 212 of the stent 200 to an adjacent outer crown facing the first end 210 of the stent 200 along a strut is greater than a longitudinal length from the outer crown facing the second end 212 of the stent 200 to the outer crown facing the first end 210 of the stent 200, the longitudinal length being defined as parallel to the central longitudinal axis CLA of the stent 200. As described above, this shortened longitudinal length increases resistance to forces that may result in stent lifting, stent distortion, and/or poor stent retention, while maintaining the overall sinusoidal length of each band 208 such that stent overexpansion is not compromised.

In embodiments, not shown, the first end 210 and/or the second end 212 of the stent 200 may be formed such as to be substantially orthogonal to the central longitudinal axis CLA. Details regarding how the first end 210 and/or second end 212 of the stent 200 may be substantially orthogonal to the central longitudinal axis CLA can be found in U.S. Pat. No. 9,060,889, assigned to Medtronic Vascular, Inc., which is incorporated by reference herein in its entirety.

The wire 104, 204 of any of the embodiments described above may be any material suitable for use as a stent. For example, and not by way of limitation, the wire 104, 204 may be stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the wire 104, 204 may be formed from a cobalt alloy, such as L605 or MP35N®, Nitinol (nickel-titanium shape memory alloy), ABI (palladium-silver alloy), Elgiloy® (cobalt-chromium-nickel alloy), molybdenum-rhemium alloys, and other materials suitable for use in a stent. It is also contemplated that the wire may be formed from two or more materials that are laminated together, such as tantalum that is laminated with MP35N®. The wire 104, 204 may also have concentric layers of different materials. For example, and not by way of limitation, the wire 104, 204 may be a drawn-filled tube with an outer layer of a cobalt-chromium alloy with a platinum-iridium core disposed within the cobalt-chromium alloy for enhanced radiopacity and visibility under fluoroscope. The aforementioned materials and laminations are intended to be examples and are not intended to be limiting in any way. Further, the cross-sectional shape of wire 104, 204 may be round, oblong, D-shaped, oval, or any other suitable shape.

FIGS. 9-12 illustrate a stent 300 according to an embodiment hereof. The stent 300 includes a radially compressed configuration for delivery to the affected site of a blood vessel, as shown in FIG. 9, and a radially expanded configuration when deployed (not shown). The stent 300 is a generally tubular, open-ended structure having a first end 310 and a second end 312, and defines a lumen 302 therethrough. The stent 300 may be self-expanding or balloon expandable. In the embodiment of FIGS. 9-12, the stent 300 is a laser cut stent. A "laser cut stent" as the term is used herein can mean a stent wherein a stent pattern is cut into a tubular piece of solid material of the material used for the stent 300. Material is removed such that the remaining material forms the stent pattern as shown in FIG. 9. A "laser cut stent" also includes the stent pattern being cut into a flat piece of the material used for the stent 300, and then the flat piece of material is rolled such that longitudinal edges of the material are attached together, thereby forming the stent 300. Further, the term "laser cut stent" is not limited to laser cutting and removing the unwanted material, but other ways of removing the material may be utilized, such as, but not limited to etching.

Figure 10:
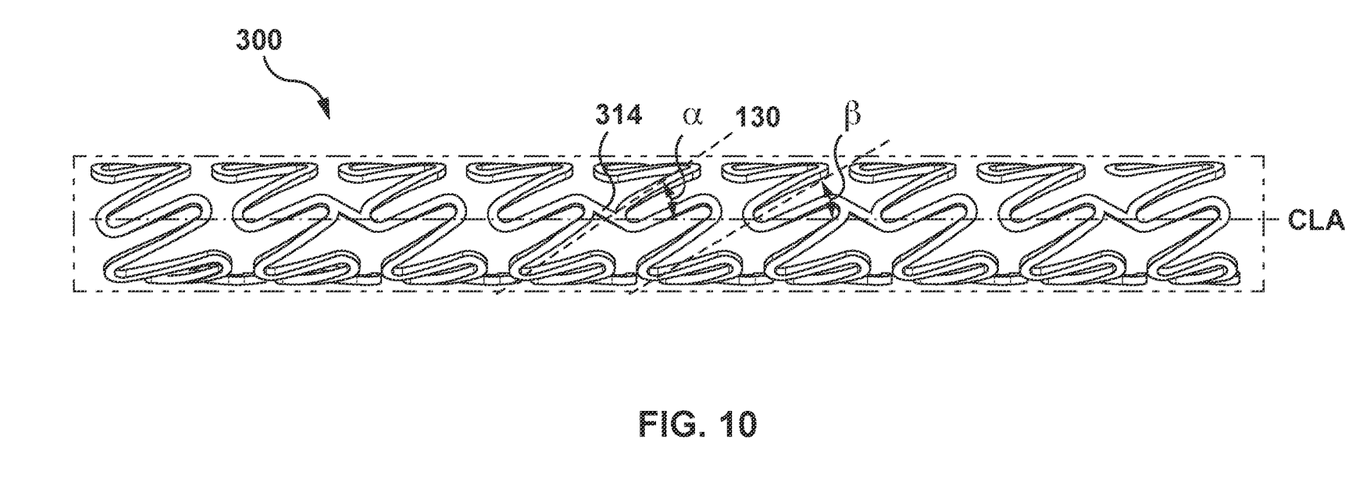
FIG. 10 is a sectional view of the stent of FIG. 9.
Figure 11:
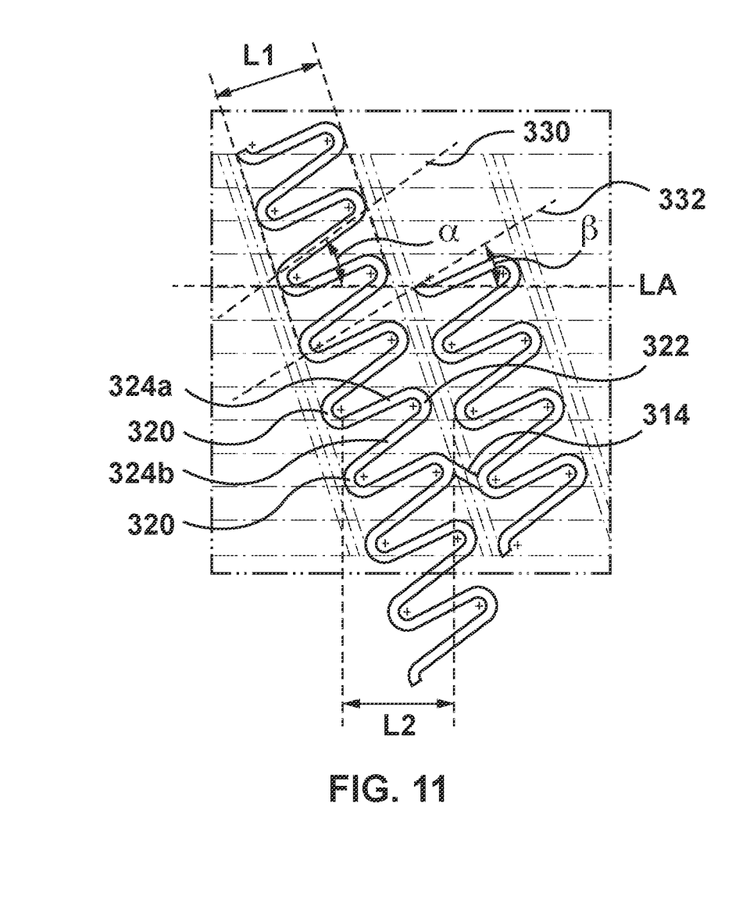
FIG. 11 illustrates a flat layout of a portion of the stent of FIG. 9.
Figure 12:
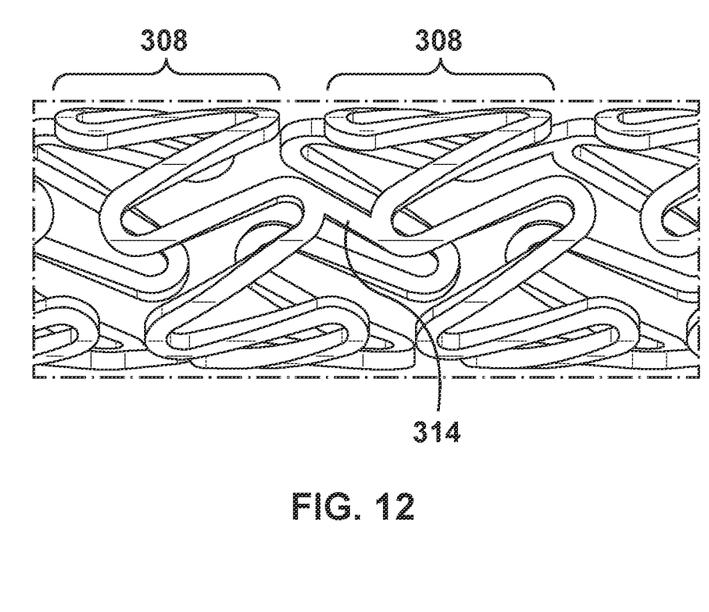
FIG. 12 illustrates a portion of the stent of FIG. 9.

The stent 300 of FIGS. 9-12 is similar to the stent 100 of FIGS. 1-4. However, rather than having a wire bent into bent into the waveform as in FIGS. 1-4, the stent 300 includes struts and crowns formed by removing material from a tubular or flat piece of material, as described above. However, the pattern of struts and crowns in FIGS. 9-12 is similar to the waveform described above with respect to FIGS. 1-4. Thus, as shown in FIGS. 9, 10, and 12, the stent pattern includes a plurality of bands 308. FIG. 9 shows nine bands 308 of the stent 300, but the stent 300 may include more or fewer bands 308. The bands 308 are generally angled with respect to a central longitudinal axis CLA of the stent 300 such that the bands 308 are not perpendicular to the central longitudinal axis CLA.

FIG. 11 shows a portion of the stent 300 cut open and laid flat such that the stent pattern can be seen. The stent pattern shown in FIG. 11 is for the central portion of the stent 300, and may also be used for the end portions of the stent 300. As best shown in FIG. 11, the stent pattern generally includes a repeating series of a first outer bend or crown 320 and a second outer bend or crown 322. The inner curve or intrados of the first outer crown 320 faces the inner curve or intrados of the second outer crown 322 such that the first outer crown 320 turns the stent pattern towards the second outer crown 322 and the second outer crown 322 turns the stent pattern towards the first outer crown 320. In other words, the inner curve or intrados of the first outer crown 320 faces the second end 312 of the stent 300 and the inner curve or intrados of the second outer crown 322 faces the first end 310 of the stent 300. A first strut 324a connects the first outer crown 320 to the second outer crown 322. A second strut 324b connects the second outer crown 322 to the first outer crown 320 in the next wave of the stent pattern. The first and second struts 324a, 324b may also be generally referred to as struts 324. Thus, a complete wave of the stent pattern in a particular order starting from one of the first outer crowns 320 is the first outer crown 320, the first strut 324a, the second outer crown 322 turning the stent pattern in a generally opposite direction, and the second strut 324b connecting to another first crown 320 in the next wave of the stent pattern. This pattern repeats itself at least though the central portion of the stent 300.

In the embodiment of FIGS. 9-12, the stent pattern of the stent 300 is such that the struts 324 are disposed at an angle α with respect to a longitudinal line LA that is parallel to the central longitudinal axis CLA of the stent 300. Thus, a line 330 that extends parallel to a strut 324 is at the angle α with respect to the line LA. Similarly, a line 332 that extends through the middle of the extrados, the middle of the intrados, and the center of radius one of the crowns 320, 322 is disposed at an angle β with respect to the line LA that is parallel central longitudinal axis CLA of the stent 300. A corresponding line 332 exists for each of the crowns 320, 322 such that each of the crowns 320, 322 are disposed at the angle β with respect to a line that is parallel to the central longitudinal axis CLA of the stent 300. As can be seen in FIGS. 10 and 11, those skilled in the art will recognize that the line LA can be the same line or different lines that are parallel to the central longitudinal axis CLA. The angle α and the angle β are approximately the same, but not necessarily exactly the same. In embodiments, the angles α and β are within about 8 degrees of each other. The angles α and β are each in the range of about 15 degrees to about 35 degrees, and preferably in the range of about 25 degrees to about 30 degrees.

As noted in the Background section above, a trade-off in using thinner profile struts in a stent is the increased risk of stent lifting and stent distortion, and reduced stent retention. However, using the highly angled struts 324 and crowns 320, 122 described above, stent lifting and stent distortion may be reduced. As can be seen in FIG. 11, a length L1 from one of the first outer crowns 320 to an adjacent one of the second outer crowns 322 along a strut 324 is greater than a longitudinal length L2 from the first outer crown 320 to the second outer crown 322, the longitudinal length L2 being defined as parallel to the central longitudinal axis CLA of the stent 300. This shortened longitudinal length L2 increases resistance to forces that may result in stent lifting, stent distortion, and/or poor stent retention, while maintaining the overall sinusoidal length of each band 308 such that stent overexpansion is not compromised.

Referring to FIGS. 10 and 12, the stent 300 also includes a plurality of connections 314 that are configured to connect selected outer crowns of 320, 322 of a band 308 with selected outer crowns 322, 320 of an adjacent band 308. The connections 314 in the embodiment of FIGS. 9-12 may be similar to struts in that they are elongated pieces of the material used to form the stent 300. In other words, the material around the connections 314 is removed from the tube or flat piece of material leaving the connections 314 as is done with the struts 324 and crowns 320, 322 of the stent 300. Using connections 314 in a laser cut stent allows for more flexibility in design of the connections 314. For example, the connections 314 may be longer and thinner, thereby increasing flexibility of the stent 300 as compared to the welded connections 114 of the embodiment of FIGS. 1-4. Further, various patterns other than the straight connections 314 shown in FIGS. 9-12 may be used, such as curved connections 314. Still further, the connections 314 need not be to immediately adjacent crowns 320, 322. Instead, in some embodiments, the connections 314 may extend at a greater angle with respect to the central longitudinal axis CLA than shown such that the connection extends more in a circumferential direction than is shown.

The material for the stent 300 may be any material suitable for use as a stent. For example, and not by way of limitation, the material for the stent 300 may be stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the wire 104, 204, 304, 404 may be formed from a cobalt alloy, such as L605 or MP35N®, Nitinol (nickel-titanium shape memory alloy), ABI (palladium-silver alloy), Elgiloy® (cobalt-chromium-nickel alloy), molybdenum-rhemium alloys, and other materials suitable for use in a stent. It is also contemplated that the wire may be formed from two or more materials that are laminated together, such as tantalum that is laminated with MP35N®. The material may also include layers of different materials. For example, and not by way of limitation, the multiple concentric tubes may be used to form the stent 300 with an outer layer of a cobalt-chromium alloy, a platinum-iridium middle layer, and a cobalt-chromium alloy inner layer such that the platinum-iridium middle layer provides enhanced radiopacity and visibility under fluoroscope. The aforementioned materials and laminations are intended to be examples and are not intended to be limiting in any way. Further, the cross-sectional shape of the struts 324, crowns 320, 322, and connections 314 of the stent 300 may be round, oblong, D-shaped, oval, or any other suitable shape.

Further, while not described in detail herein, the pattern of the stent 200 can be formed in a laser-cut stent as described with respect to stent 300. In such an embodiment, the connections between adjacent bands would be similar to the connections 314 instead of the connections 214.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent including a radially compressed configuration and a radially expanded configuration, the stent in the radially compressed configuration comprising:

a plurality of first outer crowns and second outer crowns, each of the first outer crowns and second outer crowns connected by a strut of a plurality of struts, wherein the plurality of first outer crowns includes angled first outer crowns and parallel first outer crowns and the plurality of second outer crowns includes angled second outer crowns and parallel second outer crowns; and a plurality of mid-crowns, each mid-crown disposed on a strut of the plurality of struts connecting a parallel first outer crown of the plurality of parallel first outer crowns and an angled second outer crown of the plurality of angled second outer crowns or on a strut of the plurality of struts connecting a parallel second outer crown of the parallel second outer crowns and an angled first outer crown of the angled first outer crowns;

wherein the angled first outer crowns and the angled second outer crowns are disposed at a crown angle in the range of about 15 degrees to about 35 degrees, the crown angle being defined by a line extending through a midpoint of a crown of the angled first outer crowns or the angled second outer crowns and through a center of radius of the crown with respect to a line that is parallel to a central longitudinal axis of the stent, wherein the parallel first outer crowns and the parallel second outer crowns are disposed parallel to the central longitudinal axis of the stent, and wherein the stent comprises a waveform comprising a repeating series of a first parallel first outer crown, a first angled second outer crown, a first mid-crown disposed between the first parallel first outer crown and the first angled second outer crown, a first parallel strut coupling the first parallel first outer crown to the first mid-crown, a first angled strut connecting the first mid-crown to the first angled second outer crown, a first angled first outer crown facing opposite the first angled second outer crown, a second angled strut connecting the first angled second outer crown to the first angled first outer crown, a second angled second outer crown facing opposite the first angled first outer crown, a third angled strut connecting the first angled first outer crown to the second angled second outer crown, a second angled first outer crown facing opposite the second angled second outer crown, a fourth angled strut connecting the second angled second outer crown to the second angled first outer crown, a first parallel second outer crown facing opposite the first parallel first outer crown, a second mid-crown disposed between the second angled first outer crown and the first parallel second outer crown, a fifth angled strut coupling the second angled first outer crown to the second mid-crown, a second parallel strut coupling the second mid-crown to the first parallel second outer crown, a third parallel strut coupling first parallel second outer crown a third mid-crown, a sixth angled strut coupling the third mid-crown to a third angled first outer crown, a seventh angled strut coupling the third angled first outer crown to a third angled second outer crown, and an eighth angled strut coupling the third angled second outer crown to a next wave of the waveform.

2. The stent of claim 1, wherein the crown angle is in the range of about 25 degrees to about 30 degrees.

3. The stent of claim 1, wherein the stent includes a plurality of bands including the waveform.

4. The stent of claim 3, further comprising connections between adjacent bands of the plurality of bands.

5. The stent of claim 4, wherein each connection is between one of the parallel first outer crowns of a band of the plurality of bands and one of the parallel second outer crowns of an adjacent band of the plurality of bands.

6. The stent of claim 5, wherein the stent is a continuous wire stent and the plurality of connections are fused connections, welded connections, or soldered connections.

7. The stent of claim 5, wherein the stent is a laser cut stent and the plurality of connections are elongated.

* * * * *